(12) United States Patent
Takemoto et al.

(10) Patent No.: US 6,265,524 B1
(45) Date of Patent: Jul. 24, 2001

(54) PROCESS FOR THE PREPARATION OF AROMATIC POLYCARBONATE

(75) Inventors: Hidemi Takemoto; Toru Sawaki; Katsushi Sasaki, all of Iwakuni (JP)

(73) Assignees: Teijin Limited, Osaka; UBE Industries, Ltd., Yamaguchi, both of (JP)

( * ) Notice: Subject to any disclaimer, the term of this patent is extended or adjusted under 35 U.S.C. 154(b) by 0 days.

(21) Appl. No.: 09/424,318

(22) PCT Filed: May 25, 1998

(86) PCT No.: PCT/JP98/02276

§ 371 Date: Nov. 22, 1999

§ 102(e) Date: Nov. 22, 1999

(87) PCT Pub. No.: WO98/54240

PCT Pub. Date: Dec. 3, 1998

(30) Foreign Application Priority Data

May 26, 1997 (JP) .................................................. 9-134864
May 26, 1997 (JP) .................................................. 9-134865

(51) Int. Cl.[7] .................................................. C08G 64/00
(52) U.S. Cl. ............................................................. 528/196
(58) Field of Search .............................................. 528/196

(56) References Cited

U.S. PATENT DOCUMENTS

| | | | |
|---|---|---|---|
| 5,026,817 | * 6/1991 | Sakashita et al. | 528/199 |
| 5,097,002 | * 3/1992 | Sakashita et al. | 528/199 |
| 5,142,018 | * 8/1992 | Sakashita et al. | 528/199 |
| 5,648,510 | * 7/1997 | Harada et al. | 558/274 |
| 5,892,091 | * 4/1999 | Harada et al. | 558/270 |
| 5,922,827 | * 7/1999 | Nishihira et al. | 528/196 |

FOREIGN PATENT DOCUMENTS

| | | |
|---|---|---|
| 38-1373 | 2/1963 | (JP) . |
| 2-175722 | 7/1990 | (JP) . |
| 8-333307 | 12/1996 | (JP) . |

* cited by examiner

Primary Examiner—Terressa M. Boykin
(74) Attorney, Agent, or Firm—Sughrue, Mion, Zinn, Macpeak & Seas, PLLC

(57) ABSTRACT

A process for producing an aromatic polycarbonate through an ester interchange reaction between an aromatic carbonic acid diester and an aromatic dihydroxy compound, wherein the aromatic carbonic acid diester is obtained through the decarbonylation reaction of an aromatic oxalic acid diester represented by the following general formula (1):

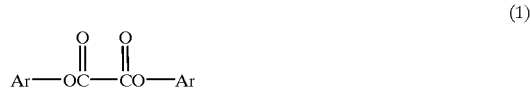

(1)

wherein two Ar's are the same or different aromatic hydrocarbon groups having 6 to 14 carbon atoms, and has a hydrolyzable halogen content of 5 ppm or less.

According to the present invention, an aromatic polycarbonate having a high molecular weight and excellent color can be easily produced without impairing ester interchange reactivity for the production of the aromatic polycarbonate by using an aromatic carbonic acid diester obtained through the decarbonylation of an aromatic oxalic acid diester and controlling the amount of hydrolyzable halogen contained in the aromatic carbonic acid diester to a value smaller than a predetermined value.

16 Claims, No Drawings

PROCESS FOR THE PREPARATION OF AROMATIC POLYCARBONATE

FIELD OF THE INVENTION

This invention relates to an economically advantageous process for producing polycarbonate having a high molecular weight and excellent color. More specifically, it relates to a process for producing polycarbonate through an ester interchange reaction between an aromatic dihydroxy compound and an aromatic carbonic acid diester produced by a specific process.

PRIOR ART

Polycarbonate is widely used for such applications as optical disks, mechanical parts and the like due to its excellent transparency, mechanical properties and thermal properties.

As a conventional industrial process for producing such polycarbonate, an interfacial polycondensation process in which an aromatic dihydroxy compound is reacted with phosgene and one in which an ester interchange reaction between an aromatic dihydroxy compound and an aromatic carbonic acid diester typified by diphenyl carbonate is carried out in a molten state are widely used.

To produce polycarbonate through an ester interchange reaction between an aromatic dihydroxy compound and an aromatic carbonic acid diester, an ester interchange catalyst typified by a basic compound is used to perform ester interchange in a molten state while heating at a temperature of 160 to 300° C., and the reaction product is directly pelletized after the completion of the reaction to produce a product. Therefore, this process is simpler and more economical than the interfacial polycondensation process.

An aromatic carbonic acid diester is generally produced through a dehydrochlorination reaction between an aromatic monohydroxy compound and phosgene, that is, so-called phosgene process. This process, however, involves safety and environmental problems because of the use of phosgene. Further, since the obtained aromatic carbonic acid diester contains an organic acid typified by phenyl chloroformate as a reaction intermediate, an ester interchange reaction is impeded when an aromatic polycarbonate is to be produced through the ester interchange reaction. Therefore, purification for removing the organic acid, for example, purification by washing with hot water as disclosed by JP-B 38-1373 (the term "JP-B" as used herein means an "examined Japanese patent publication"), must be carried out.

An aromatic carbonic acid diester obtained through an ester interchange reaction between an alkyl carbonate typified by dimethyl carbonate and an aromatic monohydroxy compound without using phosgene increases the costs of an aromatic carbonic acid diester due to its low reaction yield, which induces an increase in the costs of the obtained aromatic polycarbonate. Therefore, it is not practical. However, since it does not contain an organic acid as a reaction intermediate unlike the above aromatic carbonic acid diester obtained by using phosgene, the need for washing with hot water to remove the organic acid is low and simple purification such as distillation may be carried out.

As a process for obtaining an aromatic carbonic acid diester at a low cost without using phosgene, JP-A 8-333307 (the term "JP-A" as used herein means an "unexamined published Japanese patent application") proposes a process for obtaining an aromatic carbonic acid diester through the decarbonylation reaction of an aromatic oxalic acid diester.

Although the aromatic oxalic acid diester can be produced through an ester interchange reaction between an alkyl oxalate typified by dimethyl oxalate and an aromatic monohydroxy compound, the reaction rate of an ester interchange reaction between an alkyl oxalate and an aromatic monohydroxy compound is extremely high. Further, the yield of an aromatic carbonic acid diester produced through the decarbonylation reaction of an aromatic oxalic acid diester is also high. Consequently, an aromatic carbonic acid diester can be produced by the above process at a low cost.

In the decarbonylation reaction of an aromatic oxalic acid diester described in the above publication, an organic phosphorus compound is used as a catalyst. Typical examples of the organic phosphorus compound include phosphonium salts, phosphine, phosphine dihalide and phosphine oxide. Phosphonium halide, phosphine dihalide and a combination of phosphine or phosphine oxide and a halogen compound are preferred as a catalyst. In the decarbonylation reaction described in the above publication, an organic phosphorus compound containing halogen is inevitably used to obtain an aromatic carbonic acid diester at a high yield.

An aromatic carbonic acid diester produced through the above decarbonylation reaction does not contain an organic acid as a reaction intermediate impurity unlike an aromatic carbonic acid diester synthesized by the phosgene process. However, according to studies conducted by the inventors of the present invention, it has been revealed that when an aromatic polycarbonate is produced through an ester interchange reaction between an aromatic carbonic acid diester obtained by the above decarbonylation reaction and an aromatic dihydroxy compound, the obtained aromatic polycarbonate does not have a sufficiently high molecular weight and satisfactory color.

Problems that the Invention tries to Solve

The present inventors have conducted intensive studies to produce an aromatic polycarbonate having a high molecular weight and excellent color from an aromatic carbonic acid diester obtained through the above decarbonylation reaction and an aromatic dihydroxy compound and have found that it is effective in producing the aromatic polycarbonate to control the content of hydrolyzable halogen contained in the aromatic carbonic acid diester to a value lower than a predetermined value. The present invention has been accomplished based on this finding.

Means for Solving the Problem

That is, according to the present invention, there is provided a process for producing an aromatic polycarbonate through an ester interchange reaction between an aromatic carbonic acid diester and an aromatic dihydroxy compound, wherein the aromatic carbonic acid diester is obtained through the decarbonylation reaction of an aromatic oxalic acid diester represented by the following general formula (1):

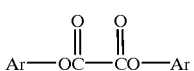

(1)

wherein two Ar's are the same or different aromatic hydrocarbon groups having 6 to 14 carbon atoms, and contains 5 ppm or less of hydrolyzable halogen.

The process for producing an aromatic polycarbonate according to the present invention will be described in detail hereinafter.

In the present invention, the aromatic polycarbonate is produced through an ester interchange reaction between an aromatic dihydroxy compound and an aromatic carbonic acid diester, and a characteristic feature is that there is used the aromatic carbonic acid diester obtained through the decarbonylation reaction of an aromatic oxalic acid diester represented by the above general formula (1).

The aromatic dihydroxy compound may be one which is generally used as a dihydroxy component of an aromatic polycarbonate. More specifically, an aromatic dihydroxy compound represented by the following general formula (3) is used.

(3)

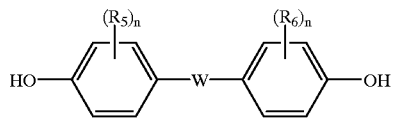

wherein W is —O—, —S—, —SO—, —SO$_2$—,

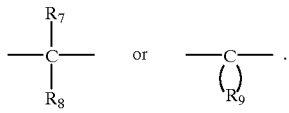

In the above general formula (3), n is an integer of 0 to 4, $R_5$ and $R_6$ are the same or different and each a halogen atom or hydrocarbon group having 1 to 12 carbon atoms. The halogen atom is preferably a chlorine atom, bromine atom or iodine atom. The hydrocarbon group is advantageously an aliphatic hydrocarbon group having 1 to 12 carbon atoms, preferably 1 to 5 carbon atoms, such as methyl group or ethyl group, or an aromatic hydrocarbon group having 6 to 12 carbon atoms, such as phenyl group. $R_7$ and $R_8$ are the same or different and each a halogen atom, hydrogen atom or hydrocarbon group having 1 to 12 carbon atoms. Illustrative examples of the hydrocarbon group are the same as those listed for the above $R_5$ and $R_6$. $R_9$ is an alkylene group having 3 to 8 carbon atoms.

Illustrative examples of the aromatic dihydroxy compound include bis(4-hydroxyphenyl)methane, 2,2-bis(4-hydroxyphenyl)propane, 2,2-bis(4-hydroxy-3-methylphenyl)propane, 4,4-bis(4-hydroxyphenyl)heptane, 2,2-bis(4-hydroxy-3,5-dichlorophenyl)propane, 2,2-bis(4-hydroxy-3,5-dibromophenyl)propane, bis(4-hydroxyphenyl)oxide, bis(3,5-dichloro-4-hydroxyphenyl)oxide, p,p'-dihydroxydiphenyl, 3,3'-dichloro-4,4'-dihydroxydiphenyl, bis(4-hydroxyphenyl)sulfone, resorcinol, hydroquinone, 1,4-dihydroxy-2,5-dichlorobenzene, 1,4-dihydroxy-3-methylbenzene, bis(4-hydroxyphenyl)sulfide, bis(4-hydroxyphenyl)sulfoxide, 9,9-bis(4-hydroxyphenyl)fluorene, 1,1-bis(4-hydroxyphenyl)-3,3,5-trimethylcyclohexane, and the like. Of these, 2,2-bis(4-hydroxyphenyl)propane (bisphenol A) is particularly preferred.

Meanwhile, the aromatic carbonic acid diester to be reacted with the aromatic dihydroxy compound may be one which is generally used for the production of an aromatic polycarbonate through an ester interchange process. More specifically, an aromatic carbonic acid diester represented by the following general formula (2) is used.

(2)

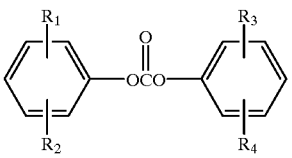

In the above general formula (2), $R_1$, $R_2$, $R_3$ and $R_4$ are the same or different and each a hydrogen atom, an alkyl group having 1 to 4 carbon atoms, a phenyl group or a halogen atom.

Illustrative examples of the aromatic carbonic acid diester include diphenyl carbonate, m-cresyl carbonate, m-cresyl phenyl carbonate, p-cresyl carbonate, p-cresyl phenyl carbonate, dinaphthyl carbonate, bis (diphenyl)carbonate, bis(chlorophenyl)carbonate and the like. Of these, diphenyl carbonate is particularly preferred.

As described above, an aromatic carbonic acid diester obtained through the decarbonylation reaction of an aromatic oxalic acid diester is used in the present invention. The aromatic oxalic acid diester is represented by the following general formula (1).

(1)

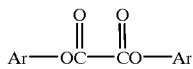

wherein two Ar's are the same or different aromatic hydrocarbon groups having 6 to 14 carbon atoms.

The aromatic oxalic acid diester represented by the above general formula (1) can also be represented by the following general formula (1') in relation to the general formula (2) since an aromatic carbonic acid diester represented by the above general formula (2) is formed by the decarbonylation reaction of the aromatic oxalic acid diester.

(1')

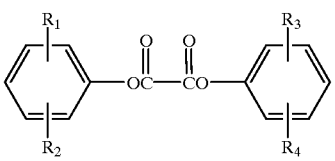

wherein $R_1$, $R_2$, $R_3$ and $R_4$ are the same as defined in the above general formula (2).

Aromatic oxalic acid diester compounds include, for example, diphenyl oxalate, m-cresyl oxalate, m-cresyl phenyl oxalate, p-cresyl oxalate, p-cresyl phenyl oxalate, dinaphthyl oxalate, bis(diphenyl)oxalate, bis(chlorophenyl) oxalate, and the like. Of these, diphenyl oxalate is particularly preferred.

An aromatic carbonic acid diester obtained through the decarbonylation reaction of an aromatic oxalic acid diester is used in the present invention. This reaction is not particularly limited but a process described in JP-A 8-333307, for example, may be used as an industrial process for inducing this reaction. The process described in this publication is excellent because of its high conversion and selectivity. According to a preferred aspect of the process described in this publication, an organic phosphorus compound such as a phosphonium salt, phosphine, phosphine dihalide or phosphine oxide is used as a catalyst. According to a number of examples described in this publication, a catalyst which makes it possible to obtain an aromatic carbonic acid diester (typically, diphenyl carbonate) at a high yield is an organic phosphorus compound containing halogen or a combination of an organic phosphorus compound and a halogen compound. Therefore, it can be said that the preferred process described by the above publication is to obtain an aromatic carbonic acid diester through the decarbonylation reaction of an aromatic oxalic acid diester using an organic phosphorus compound containing halogen (chlorine or bromine) as a catalyst.

The present inventors have produced an aromatic polycarbonate through an ester interchange reaction using an aromatic carbonic acid diester obtained through the above decarbonylation reaction, separated and purified by a commonly used method. However, when an ester interchange reaction between the aromatic carbonic acid diester obtained by the above process and an aromatic dihydroxy compound was carried out by commonly used means, the ester interchange reaction did not proceed easily and it was difficult to obtain an aromatic polycarbonate having a sufficiently high degree of polymerization after an elapse of a predetermined time. More inconveniently, was that the obtained polycarbonate was unsatisfactory in terms of color.

The present inventors have further made extensive studies on a certain compound derived from the decarbonylation reaction of the aromatic oxalic acid diester.

As a result, they paid attention to a slight amount of hydrolyzable halogen contained in the aromatic carbonic acid diester, and have found that there was correlation between the content of the hydrolyzable halogen and the molecular weight and color of the obtained polycarbonate. Although the structure and kind of the hydrolyzable halogen have not been sufficiently elucidated, it is assumed that the halogen is derived from the catalyst used in the decarbonylation reaction.

It has been revealed by the study of the present inventors that when an aromatic carbonic acid diester containing 5 ppm or less, preferably 2 ppm or less, of hydrolyzable halogen is used, an aromatic polycarbonate having an viscosity average molecular weight of 10,000 or more, preferably 15,000 or more, is obtained easily without reducing ester interchange reactivity. According to the present invention, it has been further found that a high-quality aromatic polycarbonate having a good color and a small amount of a branched polycarbonate is obtained by limiting the hydrolyzable halogen content to the above range.

To obtain an aromatic carbonic acid diester containing 5 ppm or less of hydrolyzable halogen, the aromatic carbonic acid diester is preferably subjected to a contact treatment with hot water heated to a temperature higher than the melting point of the aromatic carbonic acid diester, preferably a contact treatment with hot water having a pH of 8 to 10. These treatments may be conducted in combination, or the aromatic carbonic acid diester may be subjected to a contact treatment with hot water after purified, for example, by distillation. In addition to these methods, the hydrolyzable halogen may be removed using an adsorptive clay.

The contact treatment of the aromatic carbonic acid diester with hot water is carried out at a temperature of 80 to 120° C., preferably 80 to 100° C.

To carry out the contact treatment of the aromatic carbonic acid diester with hot water at a temperature higher than the melting point of the aromatic carbonic acid diester, the aromatic carbonic acid diester may be subjected to an ordinary interfacial extraction with neutral hot water while the aromatic carbonic acid diester is in a molten state. When hot water having a pH of 8 to 10 is used, a basic compound such as sodium carbonate, potassium carbonate, sodium hydrogencarbonate or potassium hydrogencarbonate may be used. It is preferred that 0.5 to 5 parts by weight of hot water, based on 1 part by weight of the aromatic carbonic acid diester, is used in the above contact treatment with hot water.

Further, an aromatic carbonic acid diester purified by distillation after the above contact treatment with hot water is conducted is particularly preferably used.

Although the above contact treatment with hot water and purification by distillation can be carried out once or two or more times separately, the number of times of the contact treatment and purification is determined according to the desired content of the hydrolyzable halogen and from an economical point of view.

To produce an aromatic polycarbonate by the process of the present invention, an ester interchange process known per se may be used. That is, the aromatic carbonic acid diester represented by the above general formula (2) is used in an amount of 1.005 to 1.20 mole, more preferably 1.01 to 1.10 mole, based on 1 mole of the aromatic dihydroxy compound represented by the above general formula (3).

In the present invention, the ester interchange reaction between the aromatic dihydroxy compound of the general formula (3) and the aromatic carbonic acid diester represented by the general formula (2) containing 5 ppm or less, preferably 2 ppm or less, of hydrolyzable halogen is preferably carried out in the presence of a catalyst while they are molten by heating.

As the ester interchange reaction catalyst is generally used an alkali metal compound, alkaline earth metal compound or nitrogen-containing basic compound. These catalysts will be described below.

The alkali metal compound used as a catalyst is selected from hydroxides, hydrogencarbonates, carbonates, acetates, nitrates, nitrites, sulfites, cyanates, thiocyanates, stearates, borohydrides, benzoates, hydrogen phosphates, bisphenol salts and phenol salts of alkali metals.

Illustrative examples of the alkali metal compound include sodium hydroxide, potassium hydroxide, lithium hydroxide, sodium hydrogencarbonate, potassium hydrogencarbonate, lithium hydrogencarbonate, sodium carbonate, potassium carbonate, lithium carbonate, sodium acetate, potassium acetate, lithium acetate, sodium nitrate, potassium nitrate, lithium nitrate, sodium nitrite, potassium nitrite, lithium nitrite, sodium sulfite, potassium sulfite, lithium sulfite, sodium cyanate, potassium cyanate, lithium cyanate, sodium thiocyanate, potassium thiocyanate, lithium thiocyanate, sodium stearate, potassium stearate, lithium stearate, sodium borohydride, potassium borohydride, lithium borohydride, sodium borophenylate, sodium benzoate, potassium benzoate, lithium benzoate, disodium hydrogenphosphate, dipotassium hydrogenphosphate, dilithium hydrogenphosphate; disodium salts, dipotassium salts and dilithium salts of bisphenol A; and sodium salts, potassium salts and lithium salts of phenol. Of these, sodium salts of aromatic dihydroxy compounds such as disodium salts of bisphenol A and sodium salts of aromatic monohydroxy compounds such as sodium salts of phenol are preferred.

The alkaline earth metal compound used as a catalyst is selected from calcium hydroxide, barium hydroxide, magnesium hydroxide, strontium hydroxide, calcium hydrogencarbonate, barium hydrogencarbonate, magnesium hydrogencarbonate, strontium hydrogencarbonate, calcium carbonate, barium carbonate, magnesium carbonate, strontium carbonate, calcium acetate, barium acetate, magnesium acetate, strontium acetate, calcium stearate, barium stearate, magnesium stearate, strontium stearate and the like.

The above alkali metal compound or alkaline earth metal compound is used in such an amount that a metal element contained in the catalyst is to be $1 \times 10^{-8}$ to $5 \times 10^{-5}$ equivalent, preferably $1 \times 10^{-7}$ to $5 \times 10^{-6}$ equivalent, based on one mole of the aromatic dihydroxy compound. When the amount is not in the above range, the alkali metal compound or alkaline earth metal compound may adversely affect the physical properties of the obtained polycarbonate or the ester interchange reaction may not fully proceed, thereby making it impossible to produce a high-molecular-weight polycarbonate undesirably.

The nitrogen-containing basic compound used as a catalyst is selected from ammonium hydroxides having an alkyl, aryl or alkylaryl group, such as tetramethylammonium hydroxide ($Me_4NOH$), tetraethylammonium hydroxide ($Et_4NOH$), tetrabutylammonium hydroxide ($Bu_4NOH$), benzyl trimethylammonium hydroxide ($\phi$—$CH_2(Me)_3NOH$) and hexadecyl trimethylammonium hydroxide; tertiary amines such as triethyl amine, tributyl amine, dimethylbenzyl amine, hexadecyl dimethyl amine; and basic salts such as tetramethylammonium borohydride ($Me_4NBH_4$), tetrabutylammonium borohydride ($Bu_4NBH_4$), tetrabutylammonium tetraphenyl borate ($Me_4NBPh_4$) and tetrabutylammonium tetraphenyl borate ($Bu_4NBPh_4$). Of these, tetramethylammonium hydroxide ($Me_4NOH$) is the most preferred.

The nitrogen-containing basic compound is used in an amount of $1 \times 10^{-5}$ to $1 \times 10^{-3}$ equivalent, preferably $1 \times 10^{-5}$ to $5 \times 10^{-4}$ equivalent, based on 1 mole of the aromatic dihydroxy compound.

The above ester interchange reaction catalysts may be used alone or in combination of two or more. For example, an alkali metal compound or alkaline earth metal compound and a nitrogen-containing basic compound may be used in combination. When these compounds are used in combination, the range of the catalyst is changed properly according to the ratio of the compounds.

In the ester interchange reaction of the present invention, other compounds may be used as an auxiliary catalyst as required. As such compounds may be used a catalyst used for an esterification reaction and ester interchange reaction, such as an alkali metal salt or alkaline earth metal salt of boron or aluminum hydroxide, quaternary ammonium salt, alkoxide of an alkali metal or alkaline earth metal, organic acid salt of an alkali metal or alkaline earth metal, zinc compound, boron compound, silicon compound, germanium compound, organic tin compound, lead compound, osmium compound, antimony compound, zirconium compound and the like. The present invention, however, is not limited to these. The auxiliary catalysts may be used alone or in combination of two or more.

A stabilizer may be added to the polycarbonate obtained by the process of the present invention. Known stabilizers may be used effectively as the stabilizer used in the present invention. Of these, ammonium salts and phosphonium salts of sulfonic acid are preferred, and ammonium salts and phosphonium salts of dodecylbenzenesulfonic acid such as tetrabutyl phosphonium dodecylbenzene sulfonate and ammonium salts and phosphonium salts of paratoluenesulfonic acid such as tetrabutylammonium paratoluene sulfonate are more preferred. Preferred sulfonates include methylbenzene sulfonate, ethylbenzene sulfonate, butylbenzene sulfonate, octylbenzene sulfonate, phenylbenzene sulfonate, methyl paratoluene sulfonate, ethyl paratoluene sulfonate, butyl paratoluene sulfonate, octyl paratoluene sulfonate, phenyl paratoluene sulfonate and the like, and the most preferred sulfonate is tetrabutyl phosphonium dodecylbenzene sulfonate.

The stabilizer may be used in an amount of 0.5 to 50 moles, preferably 0.5 to 10 moles, more preferably 0.8 to 5 moles, based on 1 mole of the polymerization catalyst selected from the alkali metal compound or the alkaline earth metal compound.

The stabilizer is added to and kneaded with a molten polycarbonate directly or after dissolved or dispersed in a suitable solvent. Although an apparatus used for carrying out this operation is not particularly limited, a biaxial extruder is preferred and a vented biaxial extruder is particularly preferred when the stabilizer is dissolved or dispersed in a solvent.

In the present invention, other additives may be added to polycarbonate as long as the object of the present invention can be attained. These additives are preferably added to a molten polycarbonate like in the case of a stabilizer, and include a heat stabilizer, epoxy compound, ultraviolet absorber, release agent, colorant, slipping agent, anti-blocking agent, lubricant, organic filler, inorganic filler and the like.

Of these, a heat stabilizer, ultraviolet absorber, release agent and colorant are particularly and generally used and may be used in combination of two or more.

Illustrative examples of the heat stabilizer used in the present invention include phosphorus compounds, phenolic stabilizers, organic thioether-based stabilizers, hindered amine-based stabilizers and the like.

As the ultraviolet absorber are used commonly used ultraviolet absorbers which include, for example, salicylic acid-based ultraviolet absorbers, benzophenone-based ultraviolet absorbers, benzotriazole-based ultraviolet absorbers, cyanoacrylate-based ultraviolet absorbers and the like.

As the release agent may be used generally known release agents which include, for example, hydrocarbon-based release agents such as paraffins, fatty acid-based release agents such as stearic acid, fatty acid amide-based release agents such as stearic acid amide, alcohol-based release agents such as stearyl alcohols and pentaerythritol, fatty acid ester-based release agents such as glycerin mononostearate, silicone-based release agents such as silicone oil and the like.

As the colorant may be used both organic and Inorganic pigments and dyes.

The method for adding these additives is not particularly limited, but these additives may be directly added to polycarbonate, or master pellets thereof may be prepared first, and added.

The ester interchange reaction between the aromatic dihydroxy compound and the aromatic carbonic acid diester of the present invention can be carried out by distilling out an aromatic monohydroxy compound formed by stirring them, while heating, In an inert gas atmosphere as known In the prior art. The reaction temperature is generally 120 to 350° C., preferably 160 to 300° C., and the pressure reduction rate of a reaction system is increased to 10 to 0.1 Torr in the latter stage of the reaction so as to make it easy to distill out the aromatic monohydroxy compound, thereby completing the reaction.

Effect of the Invention

According to the present invention, an aromatic polycarbonate having a high molecular weight and excellent color can be easily produced without impairing ester interchange reactivity for the production of the aromatic polycarbonate by using an aromatic carbonic acid diester obtained through the decarbonylation of an aromatic oxalic acid diester and controlling the amount of hydrolyzable halogen contained in the aromatic carbonic acid diester to a value smaller than a predetermined value.

EXAMPLES

The following examples are given to further illustrate the present invention. "%" and "parts" in the following examples mean "% by weight" and "parts by weight", unless otherwise stated, respectively. Physical properties in the following examples were measured as follows.

(1) Viscosity-Average Molecular Weight

The intrinsic viscosity of a 0.7 g/dl methylene chloride solution is measured using an Ubbellohde viscometer, and the viscosity-average molecular weight is obtained from the following equation.

$$[\eta]=1.23\times10^{-4}M^{0.83}$$

(2) Color (b Value)

The Lab value of a polycarbonate pellet (2.5 (short diameter)×3.3 (long diameter)×3.0 (length) mm) is measured by a reflection method using the ND-1001DP of Nippon Denshoku Kogyo Co., Ltd. and the b value is used as an index of yellowness. In the following Tables, "impossible" denotes that pelletization was impossible to be done because of low molecular weight of the polycarbonate and hence, the color could not be measured.

(3) Content of Hydrolyzable Halogen

The amount of halogen ions formed by the hydrolysis of hydrolyzable halogen is measured by the following method. One gram of an aromatic carbonic acid diester is dissolved into 20 ml of toluene, and the 10 ml of purified water is added, and stirred for 20 minutes to extract halogen ions into water. The amount of halogen ions contained in 50 μl of this solution is determined using 2 mM of $NaHCO_3$ as an elute and the DX500 Ion Chromatograph of Dionex Co., Ltd.

(4) Amount of Branched Polycarbonate 20 mg of polycarbonate is dissolved in 0.4 ml of chloroform-d and the branching structures of ① a phenyl salicylate type (H1 8.06 to 8.1 ppm) (H2 10.51 ppm) and ② a DPC-COOPh type (Ha 8.23 to 8.27 ppm) are measured with 270 Mz $^1$H-NMR (EX270 of JEOL LTD.) 2,048 times to determine the amount of a branched polycarbonate.

Example 1

300 parts of diphenyl oxalate was charged into a reactor equipped with a stirrer and a cooling column and 4.65 parts of tetraphenyl phosphonium chloride was added thereto as a catalyst. The temperature inside the reactor was elevated to 255° C. under normal pressure and while removing carbon monoxide gas generated outside the system, decarbonylation reaction was carried out at 255° C. for 3 hours to obtain diphenyl carbonate (DPC selectivity: 99%, DPC yield 95%). To 200 parts of this diphenyl carbonate was added 400 parts of distilled water(pure water), and the mixture was heated to 90° C. and stirred for 1 hour. A heavy solution (diphenyl carbonate layer) was separated and dried at 50° C. under a reduced pressure for 24 hours to obtain diphenyl carbonate containing 1.8 ppm of hydrolyzable chlorine, to be used in an ester interchange reaction.

100 parts of bisphenol A (of Nippon Steel Chemical Co., Ltd.), 95.7 parts of the above diphenyl carbonate, 2×10$^{-6}$ mole of sodium hydroxide and 1×10$^{-4}$ mole of tetramethylammonium hydroxide, based on 1 mole of bisphenol A, as catalysts were charged into a reactor equipped with a stirrer and distillation column, and the inside of the reactor was substituted with nitrogen. This mixture was heated to 150° C. to be molten under agitation. Thereafter, most of phenol was distilled off in 1 hour by reducing the pressure to 30 mmHg and elevating the temperature to 200° C. Then, a reaction was carried out for 2 hours by further elevating the temperature to 270° C. and reducing the pressure to 1 mmHg, and then 2 times mole to sodium catalyst of tetrabutyl phosphonium dodecylbenzene sulfonate was added as a stabilizer, and the resulting product was kneaded.

Polycarbonate having a viscosity-average molecular weight of 15,200 was obtained and cut into a pellet with a cutter. This pellet was measured for the physical properties of the polycarbonate. The conditions and results are shown in Tables I-A and I-B below.

Example 2

Washing of diphenyl carbonate, obtained through the decarbonylation reaction of diphenyl oxalate using tetraphenyl phosphonium chloride as a catalyst, with hot distilled water was repeated twice in the same manner as in Example 1 to obtain diphenyl carbonate containing 1.5 ppm of hydrolyzable chlorine. Polycarbonate was synthesized in the same manner as In Example 1 except that this diphenyl carbonate was used. A pellet of this polycarbonate was used for the measurement of its physical properties. The conditions and results are shown in Tables I-A and I-B below.

Example 3

Washing of diphenyl carbonate, obtained through the decarbonylation reaction of diphenyl oxalate using tetraphenyl phosphonium chloride as a catalyst, with hot distilled water was repeated twice in the same manner as in Example 1. The obtained diphenyl carbonate was charged into a distillation device having a packed column equipped with the 100A SULZER Packed Column CYX6 to obtain diphenyl carbonate containing 0.9 ppm of hydrolyzable chlorine at an yield of 85 % under such conditions as a bottom temperature of 200° C., a column top pressure of 20 mmHg and a reflux ratio of 5.

An ester interchange reaction between this diphenyl carbonate and bisphenol A was carried out in the same manner as in Example 1 to synthesize polycarbonate. A pellet of this polycarbonate was used for the measurement of its physical properties. The conditions and results are shown in Tables I-A and I-B below.

Example 4

400 parts of an aqueous solution of sodium hydrogencarbonate having a pH of 8 were added to 200 parts of diphenyl carbonate, obtained through the decarbonylation reaction of diphenyl oxalate using tetraphenyl phosphonium chloride as a catalyst, and the mixture was heated to 90° C. and stirred for 1 hour to obtain diphenyl carbonate containing 1.3 ppm of hydrolyzable chlorine.

An ester interchange reaction between this diphenyl carbonate and bisphenol A was carried out in the same manner as in Example 1 to synthesize polycarbonate. A pellet of this polycarbonate was used for the measurement of its physical properties. The conditions and results are shown in Tables I-A and I-B below.

Example 5

400 parts of an aqueous solution of sodium hydrogencarbonate having a pH of 8 were added to 200 parts of diphenyl carbonate, obtained through the decarbonylation reaction of diphenyl oxalate using tetraphenyl phosphonium chloride as a catalyst, and the mixture was heated to 90° C. and stirred for 1 hour. The obtained heavy solution (diphenyl carbonate layer) was purified by distillation in the same manner as in Example 3 at an yield of 85% to obtain diphenyl carbonate containing 0.8 ppm of hydrolyzable chlorine.

An ester interchange reaction between this diphenyl carbonate and bisphenol A was carried out in the same manner as in Example 1 to synthesize polycarbonate. A pellet of this polycarbonate was used for the measurement of its physical properties. The conditions and results are shown in Tables I-A and I-B below.

Example 6

An ester interchange reaction between diphenyl carbonate, containing 0.9 ppm of hydrolyzable chlorine, of Example 3 and bisphenol A was carried out in the same manner as in Example 1 except that a disodium salt of bisphenol A was used in place of sodium hydroxide as an ester interchange catalyst in an amount of $2\times10^{-6}$ mole, in terms of sodium, based on bisphenol A, to synthesize polycarbonate. A pellet of this polycarbonate was used for the measurement of its physical properties. The conditions and results are shown in Tables I-A and I-B below.

Comparative Example 1

Diphenyl carbonate, obtained through the decarbonylation reaction of diphenyl oxalate using tetraphenyl phosphonium chloride as a catalyst, contained 24 ppm of hydrolyzable chlorine. An ester interchange reaction between this diphenyl carbonate and bisphenol A was carried out in the same manner as in Example 1 to synthesize polycarbonate. The conditions and results are shown in Tables I-A and I-B below.

Comparative Example 2

Diphenyl carbonate, obtained through the decarbonylation reaction of diphenyl oxalate using tetraphenyl phosphonium chloride as a catalyst, contained 24 ppm of hydrolyzable chlorine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $2.0\times10^{-6}$ mole, in terms of sodium, based on bisphenol A, to synthesize polycarbonate. The conditions and results are shown in Tables I-A and I-B below.

Example 7

400 parts of an aqueous solution of sodium hydrogencarbonate having a pH of 10 were added to 200 parts of diphenyl carbonate, obtained through the decarbonylation reaction of diphenyl oxalate using a hydrochloride of tetraphenyl phosphonium chloride as a catalyst, and the mixture was heated to 90° C. and stirred for 1 hour. To the obtained heavy solution (diphenyl carbonate layer) was further added 400 parts of distilled water, and the resulting mixture was heated to 90° C. and stirred for 1 hour. This additional washing step was repeated twice. The resulting heavy solution was purified by distillation in the same manner as in Example 3 at an yield of 90% to obtain diphenyl carbonate containing 1.9 ppm of hydrolyzable chlorine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $1.2\times10^{-5}$ mole, in terms of sodium, based on bisphenol A, to synthesize polycarbonate. A pellet of this polycarbonate was used for the measurement of its physical properties. The conditions and results are shown in Tables I-A and I-B below.

Example 8

400 parts of an aqueous solution of sodium hydrogencarbonate having a pH of 10 were added to 200 parts of diphenyl carbonate, obtained through the decarbonylation reaction of diphenyl oxalate using a hydrochloride of tetraphenyl phosphonium chloride as a catalyst, and the mixture was heated to 90° C. and stirred for 1 hour. To the obtained heavy solution (diphenyl carbonate layer) was further added 400 parts of distilled water, and the resulting mixture was heated to 90° C. and stirred for 1 hour. This additional washing step was repeated twice to obtain diphenyl carbonate containing 3.1 ppm of hydrolyzable chlorine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $1.8\times10^{-5}$ mole, in terms of sodium, based on bisphenol A, to synthesize polycarbonate. A pellet of this polycarbonate was used for the measurement of its physical properties. The conditions and results are shown in Tables I-A and I-B below.

Example 9

400 parts of an aqueous solution of sodium hydrogencarbonate having a pH of 10 were added to 200 parts of diphenyl carbonate, obtained through the decarbonylation reaction of diphenyl oxalate using a hydrochloride of tetraphenyl phosphonium chloride as a catalyst, and the mixture was heated to 90° C. and stirred for 1 hour. To the obtained heavy solution (diphenyl carbonate layer) was further added 400 parts of distilled water, and the resulting mixture was heated to 90° C. and stirred for 1 hour. This additional washing step was repeated twice to obtain diphenyl carbonate containing 3.9 ppm of hydrolyzable chlorine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $2.4\times10^{-5}$ mole, in terms of sodium, based on bisphenol A, to synthesize polycarbonate. A pellet of this polycarbonate was used for the measurement of its physical properties. The conditions and results are shown in Tables I-A and I-B below.

Example 10

400 parts of distilled water were added to 200 parts of diphenyl carbonate, obtained through the decarbonylation reaction of diphenyl oxalate using a hydrochloride of tetraphenyl phosphonium chloride as a catalyst, and the mixture was heated to 90° C. and stirred for 1 hour. This washing step was repeated twice to obtain diphenyl carbonate containing 4.9 ppm of hydrolyzable chlorine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $3.0\times10^{-5}$ mole, in terms of sodium, based on bisphenol A, to synthesize polycarbonate. A pellet of this polycarbonate was used for the measurement of its physical properties. The conditions and results are shown in Tables I-A and I-B below.

Comparative Example 3

400 parts of distilled water were added to 200 parts of diphenyl carbonate, obtained through the decarbonylation reaction of diphenyl oxalate using a hydrochloride of tetraphenyl phosphonium chloride as a catalyst, and the mixture was heated to 90° C. and stirred for 1 hour to obtain diphenyl carbonate containing 5.8 ppm of hydrolyzable chlorine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $2.0\times10^{-6}$ mole, in terms of sodium, based on bisphenol A, to synthesize polycarbonate. A pellet of this polycarbonate was used for the measurement of its physical properties. The conditions and results are shown in Tables I-A and I-B below.

Comparative Example 4

400 parts of distilled water were added to 200 parts of diphenyl carbonate, obtained through the decarbonylation reaction of diphenyl oxalate using a hydrochloride of tetraphenyl phosphonium chloride as a catalyst, and the mixture was heated to 90° C. and stirred for 1 hour to obtain diphenyl carbonate containing 5.8 ppm of hydrolyzable chlorine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $3.0 \times 10^{-5}$ mole, in terms of sodium, based on bisphenol A, to synthesize polycarbonate. A pellet of this polycarbonate was used for the measurement of its physical properties. The conditions and results are shown in Tables I-A and I-B below.

Comparative Example 5

400 parts of distilled water were added to 200 parts of diphenyl carbonate, obtained through the decarbonylation reaction of diphenyl oxalate using a hydrochloride of tetraphenyl phosphonium chloride as a catalyst, and the mixture was heated to 90° C. and stirred for 1 hour to obtain diphenyl carbonate containing 5.8 ppm of hydrolyzable chlorine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $3.5 \times 10^{-5}$ mole, in terms of sodium, based on bisphenol A, to synthesize polycarbonate. A pellet of this polycarbonate was used for the measurement of its physical properties. The conditions and results are shown in Tables I-A and I-B below.

TABLE I-A

| | Decarbonylation catalyst | Washing with hot water (1) | | | | | Washing with hot water (2) | | | | |
|---|---|---|---|---|---|---|---|---|---|---|---|
| | | water | pH | temp. (° C.) | time (hr) | cycle | water | pH | temp. (° C.) | time (hr) | cycle |
| Example 1 | $Ph_4PCl$ | pure water | 7 | 90 | 1 | 1 | | | | | |
| Example 2 | $Ph_4PCl$ | pure water | 7 | 90 | 1 | 2 | | | | | |
| Example 3 | $Ph_4PCl$ | pure water | 7 | 90 | 1 | 2 | | | | | |
| Example 4 | $Ph_4PCl$ | $NaHCO_3$ water | 8 | 90 | 1 | 1 | | | | | |
| Example 5 | $Ph_4PCl$ | $NaHCO_3$ water | 8 | 90 | 1 | 1 | | | | | |
| Example 6 | $Ph_4PCl$ | pure water | 7 | 90 | 1 | 2 | | | | | |
| Comparative Example 1 | $Ph_4PCl$ | | | | | 0 | | | | | |
| Comparative Example 2 | $Ph_4PCl$ | | | | | 0 | | | | | |
| Example 7 | $Ph_4PCl.HCl$ | $NaHCO_3$ water | 10 | 90 | 1 | 1 | pure water | 7 | 90 | 1 | 2 |
| Example 8 | $Ph_4PCl.HCl$ | $NaHCO_3$ water | 10 | 90 | 1 | 1 | pure water | 7 | 90 | 1 | 2 |
| Example 9 | $Ph_4PCl.HCl$ | $NaHCO_3$ water | 10 | 90 | 1 | 1 | pure water | 7 | 90 | 1 | 1 |
| Example 10 | $Ph_4PCl.HCl$ | pure water | 7 | 90 | 1 | 2 | | | | | |
| Comparative Example 3 | $Ph_4PCl.HCl$ | pure water | 7 | 90 | 1 | 1 | | | | | |
| Comparative Example 4 | $Ph_4PCl.HCl$ | pure water | 7 | 90 | 1 | 1 | | | | | |
| Comparative Example 5 | $Ph_4PCl.HCl$ | pure water | 7 | 90 | 1 | 1 | | | | | |

TABLE I-B

| | Distillation | | | | diphenyl carbonate hydrolyzable halogen (ppm) | polymerization time 270° C. 1torr (hr) | polycarbonate | | |
|---|---|---|---|---|---|---|---|---|---|
| | bottom Temperature (° C.) | column top pressure (torr) | reflux ratio | yield (%) | | | viscosity average molecular weight | color (b value) | branched amount (mol %) |
| Example 1 | | | | | 1.8 | 2.0 | 15200 | 1.2 | 0.15 |
| Example 2 | | | | | 1.5 | 2.0 | 20300 | 1.2 | 0.19 |
| Example 3 | 200 | 20 | 5 | 85 | 0.9 | 2.0 | 25400 | 0.8 | 0.22 |
| Example 4 | | | | | 1.3 | 2.0 | 23300 | 1 | 0.2 |
| Example 5 | 200 | 20 | 5 | 85 | 0.8 | 2.0 | 27100 | 0.8 | 0.24 |

TABLE I-B-continued

| | Distillation | | | | diphenyl carbonate hydrolyzable halogen (ppm) | polymerization time 270° C. 1torr (hr) | polycarbonate | | |
|---|---|---|---|---|---|---|---|---|---|
| | bottom Temperature (° C.) | column top pressure (torr) | reflux ratio | yield (%) | | | viscosity average molecular weight | color (b value) | branched amount (mol %) |
| Example 6 | | | | | 0.9 | 2.0 | 25500 | 0.5 | 0.23 |
| Comparative Example 1 | | | | | 24 | 4.0 | 6000 | impossible | 0.11 |
| Comparative Example 2 | | | | | 24 | 4.0 | 6200 | impossible | 0.1 |
| Example 7 | 200 | 20 | 5 | 90 | 1.9 | 1.9 | 15300 | 0.7 | 0.14 |
| Example 8 | | | | | 3.1 | 1.9 | 15300 | 0.7 | 0.16 |
| Example 9 | | | | | 3.9 | 1.8 | 15200 | 0.9 | 0.15 |
| Example 10 | | | | | 4.9 | 1.7 | 15300 | 0.8 | 0.16 |
| Comparative Example 3 | | | | | 5.8 | 4.0 | 9800 | 2.6 | 0.27 |
| Comparative Example 4 | | | | | 5.8 | 2.0 | 15300 | 1.9 | 0.39 |
| Comparative Example 5 | | | | | 5.8 | 1.8 | 15200 | 1.7 | 0.29 |

Example 11

400 parts of an aqueous solution of sodium hydrogencarbonate having a pH of 10 were added to 200 parts of diphenyl carbonate, obtained through the decarbonylation reaction of diphenyl oxalate using a hydrochloride of tetraphenyl phosphonium chloride as a catalyst, and the mixture was heated to 90° C. and stirred for 1 hour. To the obtained heavy solution (diphenyl carbonate layer) was further added 400 parts of distilled water, and the resulting mixture was heated to 90° C. and stirred for 1 hour. This additional washing step was repeated twice. The resulting heavy solution was purified by distillation in the same manner as in Example 3 at an yield of 80% to obtain diphenyl carbonate containing 0.9 ppm of hydrolyzable chlorine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $3.0 \times 10^{-5}$ mole, in terms of sodium, based on bisphenol A, to synthesize polycarbonate. A pellet of this polycarbonate was used for the measurement of its physical properties. The conditions and results are shown in Tables II-A and II-B below.

Example 12

400 parts of an aqueous solution of sodium hydrogencarbonate having a pH of 10 were added to 200 parts of diphenyl carbonate, obtained through the decarbonylation reaction of diphenyl oxalate using a hydrochloride of tetraphenyl phosphonium chloride as a catalyst, and the mixture was heated to 90° C. and stirred for 1 hour. To the obtained heavy solution (diphenyl carbonate layer) was further added 400 parts of distilled water, and the resulting mixture was heated to 90° C. and stirred for 1 hour. This additional washing step was repeated twice. The resulting heavy solution was purified by distillation in the same manner as in Example 3 at an yield of 90% to obtain diphenyl carbonate containing 1.9 ppm of hydrolyzable chlorine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $3.0 \times 10^{-5}$ mole, in terms of sodium, based on bisphenol A, to synthesize polycarbonate. A pellet of this polycarbonate was used for the measurement of its physical properties. The conditions and results are shown in Tables II-A and II-B below.

Example 13

400 parts of an aqueous solution of sodium hydrogencarbonate having a pH of 10 were added to 200 parts of diphenyl carbonate, obtained through the decarbonylation reaction of diphenyl oxalate using a hydrochloride of tetraphenyl phosphonium chloride as a catalyst, and the mixture was heated to 90° C. and stirred for 1 hour. To the obtained heavy solution (diphenyl carbonate layer) was further added 400 parts of distilled water, and the resulting mixture was heated to 90° C. and stirred for 1 hour. This additional washing step was repeated twice to obtain diphenyl carbonate containing 3.1 ppm of hydrolyzable chlorine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $3.0 \times 10^{-5}$ mole, in terms of sodium, based on bisphenol A, to synthesize polycarbonate. A pellet of this polycarbonate was used for the measurement of its physical properties. The conditions and results are shown in Tables II-A and II-B below.

Example 14

400 parts of an aqueous solution of sodium hydrogencarbonate having a pH of 10 were added to 200 parts of diphenyl carbonate, obtained through the decarbonylation reaction of diphenyl oxalate using a hydrochloride of tetraphenyl phosphonium chloride as a catalyst, and the mixture was heated to 90° C. and stirred for 1 hour. To the obtained heavy solution (diphenyl carbonate layer) was further added 400 parts of distilled water, and the resulting mixture was heated to 90° C. and stirred for 1 hour to obtain diphenyl carbonate containing 3.9 ppm of hydrolyzable chlorine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $3.0 \times 10^{-5}$ mole, in terms of sodium, based on bisphenol A, to synthesize polycarbonate. A pellet of this polycarbonate was used for the measurement of its physical properties. The conditions and results are shown in Tables II-A and II-B below.

Comparative Example 6

Diphenyl carbonate, obtained through the decarbonylation reaction of diphenyl oxalate using a hydrochloride of tetraphenyl phosphonium chloride as a catalyst, contained 39 ppm of hydrolyzable chlorine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $3.0 \times 10^{-5}$ mole, in terms of sodium, based on bisphenol A, to synthesize polycarbonate. The conditions and results are shown in Tables II-A and II-B below.

Example 15

Washing of diphenyl carbonate, obtained through the decarbonylation reaction of diphenyl oxalate using tetraphenyl phosphonium chloride and chloroform as catalysts, with hot distilled water was repeated twice in the same manner as in Example 1. The obtained diphenyl carbonate was charged into a distillation device having a packed column equipped with the 100A SULZER Packed Column CYX6 to obtain diphenyl carbonate containing 0.9 ppm of hydrolyzable chlorine at an yield of 90% under such conditions as a bottom temperature of 200° C., a column top pressure of 20 mmHg and a reflux ratio of 5.

An ester interchange reaction between this diphenyl carbonate and bisphenol A was carried out in the same manner as in Example 1 except that a disodium salt of bisphenol A was used in place of sodium hydroxide as an ester interchange catalyst in an amount of $2.0 \times 10^{-6}$ mole, in terms of sodium, based on bisphenol A, to synthesize polycarbonate. A pellet of this polycarbonate was used for the measurement of its physical properties. The conditions and results are shown in Tables II-A and II-B below.

Example 16

Diphenyl carbonate containing 1.5 ppm of hydrolyzable chlorine was obtained in the same manner as in Example 15 except that washing with hot water was carried out only once. Polycarbonate was synthesized using this diphenyl carbonate under the same conditions as those of Example 15. A pellet of this polycarbonate was used for the measurement of its physical properties. The conditions and results are shown in Tables II-A and II-B below.

Comparative Example 7

400 parts of distilled water were added to 200 parts of diphenyl carbonate obtained through a decarbonylation reaction, and the mixture was heated to 90° C. and stirred for 1 hour. The obtained heavy solution was dried at 50° C. and a reduced pressure to obtain diphenyl carbonate containing 8.3 ppm of hydrolyzable chlorine. Polycarbonate was synthesized using this diphenyl carbonate under the same conditions as those of Example 15. A pellet of this polycarbonate was used for the measurement of its physical properties. The conditions and results are shown in Tables II-A and II-B below.

Example 17

400 parts of an aqueous solution of sodium hydrogencarbonate having a pH of 10 were added to 200 parts of diphenyl carbonate, obtained through the decarbonylation reaction of diphenyl oxalate using tetraphenyl phosphonium bromide and hydrogen chloride as catalysts, and the mixture was heated to 90° C. and stirred for 1 hour. This washing step was repeated twice. To the obtained heavy solution (diphenyl carbonate layer) was further added 400 parts of distilled water, and the resulting mixture was heated to 90° C. and stirred for 1 hour. The resulting heavy solution was purified by distillation in the same manner as in Example 3 at an yield of 90% to obtain diphenyl carbonate containing 0.5 ppm of hydrolyzable halogen. An ester interchange reaction between this diphenyl carbonate and bisphenol A was carried out in the same manner as in Example 1 except that a disodium salt of bisphenol A was used in place of sodium hydroxide as an ester interchange catalyst in an amount of $2.0 \times 10^{-6}$ mole, in terms of sodium, based on bisphenol A, to synthesize polycarbonate. A pellet of this polycarbonate was used for the measurement of its physical properties. The conditions and results are shown in Tables II-A and II-B below.

Example 18

400 parts of an aqueous solution of sodium hydrogencarbonate having a pH of 10 were added to 200 parts of diphenyl carbonate, obtained through the decarbonylation reaction of diphenyl oxalate using tetraphenyl phosphonium bromide and hydrogen chloride as catalysts, and the mixture was heated to 90° C. and stirred for 1 hour. This washing step was repeated twice. To the obtained heavy solution (diphenyl carbonate layer) was further added 400 parts of distilled water, and the resulting mixture was heated to 90° C. and stirred for 1 hour to obtain diphenyl carbonate containing 1.5 ppm of hydrolyzable halogen. An ester interchange reaction between this diphenyl carbonate and bisphenol A was carried out in the same manner as in Example 1 except that a disodium salt of bisphenol A was used in place of sodium hydroxide as an ester interchange catalyst in an amount of $2.0 \times 10^{-6}$ mole, in terms of sodium, based on bisphenol A, to synthesize polycarbonate. A pellet of this polycarbonate was used for the measurement of its physical properties. The conditions and results are shown in Tables II-A and II-B below.

Comparative Example 8

400 parts of an aqueous solution of sodium hydrogencarbonate having a pH of 10 were added to 200 parts of diphenyl carbonate, obtained through the decarbonylation reaction of diphenyl oxalate using tetraphenyl phosphonium bromide and hydrogen chloride as catalysts, and the mixture was heated to 90° C. and stirred for 1 hour to obtain diphenyl carbonate containing 9.1 ppm of hydrolyzable halogen. An ester interchange reaction between this diphenyl carbonate and bisphenol A was carried out in the same manner as in Example 1 except that a disodium salt of bisphenol A was used in place of sodium hydroxide as an ester interchange catalyst in an amount of $2.0 \times 10^{-6}$ mole, in terms of sodium, based on bisphenol A, to synthesize polycarbonate. A pellet of this polycarbonate was used for the measurement of its physical properties. The conditions and results are shown in Tables II-A and II-B below.

TABLE II-A

|  | Decarbonylation catalyst |  | Washing with hot water (1) | | | | | Washing with hot water (2) | | | | |
| --- | --- | --- | --- | --- | --- | --- | --- | --- | --- | --- | --- | --- |
|  |  |  | water | pH | temp. (° C.) | time (hr) | cycle | water | pH | temp. (° C.) | time (hr) | cycle |
| Example 11 | Ph$_4$PCl.HCl |  | NaHCO$_3$ water | 10 | 90 | 1 | 1 | pure water | 7 | 90 | 1 | 2 |
| Example 12 | Ph$_4$PCl.HCl |  | NaHCO$_3$ water | 10 | 90 | 1 | 1 | pure water | 7 | 90 | 1 | 2 |
| Example 13 | Ph$_4$PCl.HCl |  | NaHCO$_3$ water | 10 | 90 | 1 | 1 | pure water | 7 | 90 | 1 | 2 |
| Example 14 | Ph$_4$PCl.HCl |  | NaHCO$_3$ water | 10 | 90 | 1 | 1 | pure water | 7 | 90 | 1 | 1 |
| Comparative Example 6 | Ph$_4$PCl.HCl |  |  |  |  |  | 0 |  |  |  |  |  |
| Example 15 | Ph$_4$PCl | CHCl$_3$ | pure water | 7 | 90 |  | 2 |  |  |  |  |  |
| Example 16 | Ph$_4$PCl | CHCl$_3$ | pure water | 7 | 90 |  | 1 |  |  |  |  |  |
| Comparative Example 7 | Ph$_4$PCl | CHCl$_3$ | pure water | 7 | 90 |  | 1 |  |  |  |  |  |
| Example 17 | Ph$_4$PBr | HCl | NaHCO$_3$ water | 10 | 90 |  | 2 | pure water | 7 | 90 | 1 | 1 |
| Example 18 | Ph$_4$PBr | HCl | NaHCO$_3$ water | 10 | 90 |  | 2 | pure water | 7 | 90 | 1 | 1 |
| Comparative Example 8 | Ph$_4$PBr | HCl | NaHCO$_3$ water | 10 | 90 |  | 1 | pure water | 7 | 90 | 1 | 1 |

TABLE II-B

|  | Distillation | | | | diphenyl carbonate hydrolyzable halogen (ppm) | polymer ization time 270° C. 1torr (hr) | polycarbonate | | |
| --- | --- | --- | --- | --- | --- | --- | --- | --- | --- |
|  | bottom Temperature (° C.) | column top pressure (torr) | reflux ratio | yield (%) |  |  | viscosity average molecular weight | color (b value) | branched amount (mol %) |
| Example 11 | 200 | 20 | 5 | 80 | 0.9 | 1.1 | 15300 | 0.6 | 0.24 |
| Example 12 | 200 | 20 | 5 | 90 | 1.9 | 1.2 | 15200 | 0.8 | 0.23 |
| Example 13 |  |  |  |  | 3.1 | 1.7 | 15300 | 0.8 | 0.2 |
| Example 14 |  |  |  |  | 3.9 | 1.6 | 15200 | 0.9 | 0.2 |
| Comparative Example 6 |  |  |  |  | 39 | 4.0 | 6900 | impossible | 0.11 |
| Example 15 | 200 | 20 | 5 | 90 | 0.9 | 1.0 | 15200 | 0.8 | 0.12 |
| Example 16 | 200 | 20 | 5 | 90 | 1.5 | 1.3 | 15300 | 1.1 | 0.16 |
| Comparative Example 7 |  |  |  |  | 8.3 | 4.0 | 9500 | 2.9 | 0.33 |
| Example 17 | 200 | 20 | 5 | 90 | 0.5 | 0.6 | 15200 | 0.8 | 0.1 |
| Example 18 |  |  |  |  | 1.5 | 0.8 | 15300 | 0.8 | 0.11 |
| Comparative Example 8 |  |  |  |  | 9.1 | 3.7 | 15300 | 3.3 | 0.55 |

Example 19

400 parts of an aqueous solution of sodium hydrogencarbonate having a pH of 10 were added to 200 parts of diphenyl carbonate, obtained through the decarbonylation reaction of diphenyl oxalate using triphenyl phosphine oxide and oxalyl chloride as catalysts, and the mixture was heated to 90° C. and stirred for 1 hour. This washing step was repeated twice. To the obtained heavy solution (diphenyl carbonate layer) was further added 400 parts of distilled water, and the resulting mixture was heated to 90° C. and stirred for 1 hour. The resulting heavy solution was purified by distillation in the same manner as in Example 3 at an yield of 90% to obtain diphenyl carbonate containing 1.1 ppm of hydrolyzable chlorine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $2.0 \times 10^{-6}$ mole, in terms of sodium, based on bisphenol A, to synthesize polycarbonate. A pellet of this polycarbonate was used for the measurement of its physical properties. The conditions and results are shown in Tables III-A and III-B below.

Example 20

400 parts of an aqueous solution of sodium hydrogencarbonate having a pH of 10 were added to 200 parts of diphenyl carbonate, obtained through the decarbonylation reaction of diphenyl oxalate using triphenyl phosphine oxide and oxalyl chloride as catalysts, and the mixture was heated to 90° C. and stirred for 1 hour. This washing step was repeated twice. To the obtained heavy solution (diphenyl carbonate layer) was further added 400 parts of distilled water, and the resulting mixture was heated to 90° C. and stirred for 1 hour to obtain diphenyl carbonate containing 2.1 ppm of hydrolyzable chlorine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $2.0 \times 10^{-6}$ mole, in terms of sodium, based on bisphenol A, to synthesize polycarbonate. A pellet of this polycarbonate was used for the measurement of its physical properties. The conditions and results are shown in Tables III-A and III-B below.

Comparative Example 9

400 parts of an aqueous solution of sodium hydrogencarbonate having a pH of 10 were added to 200 parts of diphenyl carbonate, obtained through the decarbonylation reaction of diphenyl oxalate using triphenyl phosphine oxide and oxalyl chloride as catalysts, the mixture was heated to 90° C. and stirred for 1 hour. To the obtained heavy solution (diphenyl carbonate layer) was further added 400 parts of distilled water, and the resulting mixture was heated to 90° C. and stirred for 1 hour to obtain diphenyl carbonate containing 10.3 ppm of hydrolyzable chlorine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $2.0 \times 10^{-6}$ mole, in terms of sodium, based on bisphenol A, to synthesize polycarbonate. The conditions and results are shown in Tables III-A and III-B below.

Example 21

400 parts of distilled water were added to 200 parts of diphenyl carbonate, obtained through the decarbonylation reaction of diphenyl oxalate using triphenyl phosphine and chloroform as catalysts, and the mixture was heated to 90° C. and stirred for 1 hour. The obtained heavy solution (diphenyl carbonate layer) was purified by distillation in the same manner as in Example 3 at an yield of 90% to obtain diphenyl carbonate containing 0.9 ppm of hydrolyzable chlorine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $2.0 \times 10^{-6}$ mole, in terms of sodium, based on bisphenol A, to synthesize polycarbonate. A pellet of this polycarbonate was used for the measurement of its physical properties. The conditions and results are shown in Tables III-A and III-B below.

Example 22

400 parts of distilled water were added to 200 parts of diphenyl carbonate, obtained through the decarbonylation reaction of diphenyl oxalate using triphenyl phosphine and chloroform as catalysts, and the mixture was heated to 90° C. and stirred for 1 hour to obtain diphenyl carbonate containing 1.8 ppm of hydrolyzable chlorine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $2.0 \times 10^{-6}$ mole, in terms of sodium, based on bisphenol A, to synthesize polycarbonate. A pellet of this polycarbonate was used for the measurement of its physical properties. The conditions and results are shown in Tables III-A and III-B below.

Comparative Example 10

Diphenyl carbonate, obtained through the decarbonylation reaction of diphenyl oxalate using triphenyl phosphine and chloroform as catalysts, contained 15 ppm of hydrolyzable chlorine. An ester interchange reaction between this diphenyl carbonate and bisphenol A was carried out in the same manner as in Example 21 to synthesize polycarbonate. A pellet of this polycarbonate was used for the measurement of its physical properties. The conditions and results are shown in Tables III-A and III-B below.

Example 23

400 parts of distilled water were added to 200 parts of diphenyl carbonate, obtained through the decarbonylation reaction of diphenyl oxalate using triphenyl phosphine and bromine ($Br_2$) as catalysts, and the mixture was heated to 90° C. and stirred for 1 hour. This washing step was repeated twice. The obtained heavy solution (diphenyl carbonate layer) was purified by distillation in the same manner as in Example 3 at an yield of 85% to obtain diphenyl carbonate containing 0.7 ppm of hydrolyzable bromine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $2.0 \times 10^{-6}$ mole, in terms of sodium, based on bisphenol A, to synthesize polycarbonate. A pellet of this polycarbonate was used for the measurement of its physical properties. The conditions and results are shown in Tables III-A and III-B below.

Example 24

400 parts of distilled water were added to 200 parts of diphenyl carbonate, obtained through the decarbonylation reaction of diphenyl oxalate using triphenyl phosphine and bromine ($Br_2$) as catalysts, and the mixture was heated to 90° C. and stirred for 1 hour. This washing step was repeated twice to obtain diphenyl carbonate containing 1.7 ppm of hydrolyzable bromine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $2.0 \times 10^{-6}$ mole, in terms of sodium, based on bisphenol A, to synthesize polycarbonate. A pellet of this polycarbonate was used for the measurement of its physical properties. The conditions and results are shown in Tables III-A and III-B below.

Comparative Example 11

Washing with hot distilled water was carried out only once in the same manner as in Example 24 to obtain diphenyl carbonate containing 7.3 ppm of hydrolyzable bromine. Polycarbonate was obtained using this diphenyl carbonate under the same conditions as in Example 24. The conditions and results are shown in Tables III-A and III-B below.

Example 25

400 parts of an aqueous solution of sodium hydrogencarbonate having a pH of 10 were added to 200 parts of diphenyl carbonate, obtained through the decarbonylation reaction of diphenyl oxalate using triphenyl phosphine and aluminum chloride as catalysts, the mixture was heated to 90° C. and stirred for 1 hour. To the obtained heavy solution (diphenyl carbonate layer) was further added 400 parts of distilled water, and the resulting mixture was heated to 90° C. and stirred for 1 hour. This additional washing step was repeated twice. The resulting heavy solution was purified by distillation in the same manner as in Example 3 at an yield of 85% to obtain diphenyl carbonate containing 1.1 ppm of hydrolyzable chlorine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $2.0 \times 10^{-6}$ mole, in terms of sodium, based on bisphenol A, to synthesize polycarbonate. A pellet of this polycarbonate was used for the measurement of its physical properties. The conditions and results are shown in Tables III-A and III-B below.

Example 26

400 parts of an aqueous solution of sodium hydrogencarbonate having a pH of 10 were added to 200 parts of diphenyl carbonate, obtained through the decarbonylation reaction of diphenyl oxalate using triphenyl phosphine and aluminum chloride as catalysts, the mixture was heated to 90° C. and stirred for 1 hour. To the obtained heavy solution (diphenyl carbonate layer) was further added 400 parts of distilled water, and the resulting mixture was heated to 90° C. and stirred for 1 hour. This additional washing step was repeated twice to obtain diphenyl carbonate containing 1.8 ppm of hydrolyzable chlorine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $2.0 \times 10^{-6}$ mole, in terms of sodium, based on bisphenol A, to synthesize polycarbonate. A pellet of this polycarbonate was used for the measurement of its physical properties. The conditions and results are shown in Tables III-A and III-B below.

Comparative Example 12

400 parts of distilled water were added to 200 parts of diphenyl carbonate, obtained through the decarbonylation reaction of diphenyl oxalate using triphenyl phosphine and aluminum chloride as catalysts, the mixture was heated to 90° C. and stirred for 1 hour. This washing step was repeated twice to obtain diphenyl carbonate containing 7.9 ppm of hydrolyzable chlorine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $2.0 \times 10^{-6}$ mole, in terms of sodium, based on bisphenol A, to synthesize polycarbonate. A pellet of this polycarbonate was used for the measurement of its physical properties. The conditions and results are shown in Tables III-A and III-B below.

Example 27

400 parts of an aqueous solution of sodium hydrogencarbonate having a pH of 8 were added to 200 parts of diphenyl carbonate, obtained through the decarbonylation reaction of diphenyl oxalate using tetraphenylphosphonium chloride as a catalyst, the mixture was heated to 90° C. and stirred for 1 hour. This washing step was repeated twice. To the obtained heavy solution (diphenyl carbonate layer) was further added 400 parts of distilled water, and the resulting mixture was heated to 90° C. and stirred for 1 hour. This additional washing step was repeated twice. The resulting heavy solution was purified by distillation in the same manner as in Example 3 at an yield of 85% to obtain diphenyl carbonate containing 0.05 ppm of hydrolyzable chlorine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $2.0 \times 10^{-6}$ mole, in terms of sodium, based on bisphenol A, to synthesize polycarbonate. A pellet of this polycarbonate was used for the measurement of its physical properties. The conditions and results are shown in Tables III-A and III-B below.

Example 28

400 parts of an aqueous solution of sodium hydrogencarbonate having a pH of 8 were added to 200 parts of diphenyl carbonate, obtained through the decarbonylation reaction of diphenyl oxalate using tetraphenylphosphonium chloride as a catalyst, the mixture was heated to 90° C. and stirred for 1 hour. This washing step was repeated twice. To the obtained heavy solution (diphenyl carbonate layer) was further added 400 parts of distilled water, and the resulting mixture was heated to 90° C. and stirred for 1 hour. This additional washing step was repeated twice. The resulting heavy solution was purified by distillation in the same manner as in Example 3 at an yield of 85% to obtain diphenyl carbonate containing 0.09 ppm of hydrolyzable chlorine. An ester interchange reaction between this diphenyl carbonate and bisphenol A was carried out in the same manner as in Example 1 except that a disodium salt of bisphenol A was used in place of sodium hydroxide as an ester interchange catalyst in an amount of $2.0 \times 10^{-6}$ mole, in terms of sodium, based on bisphenol A, to synthesize polycarbonate. A pellet of this polycarbonate was used for the measurement of its physical properties. The conditions and results are shown in Tables III-A and III-B below.

TABLE III-A

| | Decarbonylation catalyst | | water | Washing with hot water (1) | | | | Washing with hot water (2) | | | | |
| --- | --- | --- | --- | --- | --- | --- | --- | --- | --- | --- | --- | --- |
| | | | | pH | Temp. (° C.) | Time (hr) | cycle | water | pH | temp. (° C.) | time (hr) | cycle |
| Example 19 | $Ph_3P=O$ | $(COCl)_2$ | $NaHCO_3$ water | 10 | 90 | | 2 | pure water | 7 | 90 | 1 | 1 |
| Example 20 | $Ph_3P=O$ | $(COCl)_2$ | $NaHCO_3$ water | 10 | 90 | | 2 | pure water | 7 | 90 | 1 | 1 |
| Comparative Example 9 | $Ph_3P=O$ | $(COCl)_2$ | $NaHCO_3$ water | 10 | 90 | | 1 | pure water | 7 | 90 | 1 | 1 |
| Example 21 | $Ph_3P$ | $CHCl_3$ | pure water | 7 | 90 | 1 | 1 | | | | | |
| Example 22 | $Ph_3P$ | $CHCl_3$ | pure water | 7 | 90 | 1 | 1 | | | | | |

TABLE III-A-continued

|  | Decarbonylation catalyst | | Washing with hot water (1) | | | | | Washing with hot water (2) | | | | |
|---|---|---|---|---|---|---|---|---|---|---|---|---|
|  |  |  | water | pH | Temp. (° C.) | Time (hr) | cycle | water | pH | temp. (° C.) | time (hr) | cycle |
| Comparative Example 10 | Ph₃P | CHCl₃ |  |  |  |  | 0 |  |  |  |  |  |
| Example 23 | Ph₃P | Br₂ | pure water | 7 | 90 | 1 | 2 |  |  |  |  |  |
| Example 24 | Ph₃P | Br₂ | pure water | 7 | 90 | 1 | 2 |  |  |  |  |  |
| Comparative Example 11 | Ph₃P | Br₂ | pure water | 7 | 90 | 1 | 1 |  |  |  |  |  |
| Example 25 | Ph₃P | AlCl₃ | NaHCO₃ water | 10 | 90 | 1 | 1 | pure water | 7 | 90 | 1 | 2 |
| Example 26 | Ph₃P | AlCl₃ | NaHCO₃ water | 10 | 90 | 1 | 1 | pure water | 7 | 90 | 1 | 2 |
| Comparative Example 12 | Ph₃P | AlCl₃ | pure water | 7 | 90 | 1 | 2 |  |  |  |  |  |
| Example 27 | Ph₄PCl |  | NaHCO₃ water | 8 | 90 | 1 | 2 | pure water | 7 | 90 | 1 | 2 |
| Example 28 | Ph₄PCl |  | NaHCO₃ water | 8 | 90 | 1 | 2 | pure water | 7 | 90 | 1 | 2 |

TABLE III-B

|  | Distillation | | | | diphenyl carbonate hydrolyzable halogen (ppm) | polymer ization time 270° C. 1torr (hr) | polycarbonate | | |
|---|---|---|---|---|---|---|---|---|---|
|  | bottom Temperature (° C.) | column top pressure (torr) | reflux ratio | yield (%) |  |  | viscosity average molecular weight | color (b value) | branched amount (mol %) |
| Example 19 | 200 | 20 | 5 | 90 | 1.1 | 1.2 | 15300 | 1.2 | 0.12 |
| Example 20 |  |  |  |  | 2.1 | 1.4 | 15200 | 1.2 | 0.12 |
| Comparative Example 9 |  |  |  |  | 10.3 | 4.0 | 6100 | impossible | 0.22 |
| Example 21 | 200 | 20 | 5 | 90 | 0.9 | 0.7 | 15300 | 0.4 | 0.11 |
| Example 22 |  |  |  |  | 1.8 | 0.9 | 15300 | 0.9 | 0.18 |
| Comparative Example 10 |  |  |  |  | 15 | 4.0 | 10200 | 1.9 | 0.29 |
| Example 23 | 200 | 20 | 5 | 85 | 0.7 | 0.8 | 15300 | 1 | 0.17 |
| Example 24 |  |  |  |  | 1.7 | 1.0 | 15300 | 1.1 | 0.18 |
| Comparative Example 11 |  |  |  |  | 7.3 | 4.0 | 8400 | impossible | 0.41 |
| Example 25 | 200 | 20 | 5 | 85 | 1.1 | 1.1 | 15200 | 0.8 | 0.22 |
| Example 26 |  |  |  |  | 1.8 | 1.4 | 15200 | 0.6 | 0.21 |
| Comparative Example 12 |  |  |  |  | 7.9 | 4.0 | 9100 | 3.9 | 0.44 |
| Example 27 | 200 | 20 | 5 | 80 | 0.05 | 2.0 | 27500 | 1.0 | 0.25 |
| Example 28 | 200 | 20 | 5 | 85 | 0.09 | 2.0 | 25800 | 0.8 | 0.25 |

What is claimed is:

1. A process for producing an aromatic polycarbonate through an ester interchange reaction between an aromatic carbonic acid diester and an aromatic dihydroxy compound, wherein the aromatic carbonic acid diester is obtained through the decarbonylation reaction of an aromatic oxalic acid diester represented by the following general formula (1):

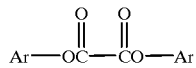

(1)

wherein two Ar's are the same or different aromatic hydrocarbon groups having 6 to 14 carbon atoms, and has a hydrolyzable halogen content of 5 ppm or less.

2. The process for producing an aromatic polycarbonate according to claim 1, wherein the aromatic carbonic acid diester contains 2 ppm or less of hydrolyzable halogen.

3. The process for producing an aromatic polycarbonate according to claim 1, wherein the aromatic carbonic acid diester is represented by the following general formula (2):

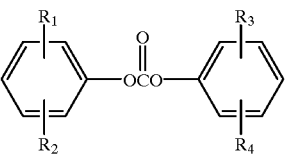

(2)

wherein $R_1$, $R_2$, $R_3$ and $R_4$ are the same or different and each a hydrogen atom, alkyl group having 1 to 4 carbon atoms, phenyl group or halogen atom.

4. The process for producing an aromatic polycarbonate according to claim 1, wherein the aromatic dihydroxy compound is represented by the following general formula (3):

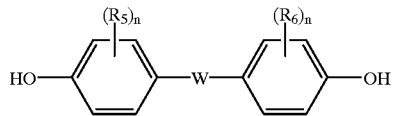

(3)

wherein W is —O—, —S—, —SO—, —SO$_2$—,

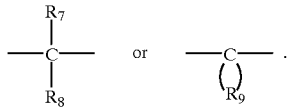

wherein n is 0 to 4, $R_5$ and $R_6$ are the same or different and each a halogen atom or a hydrocarbon group having 1 to 12 carbon atoms, $R_7$ and $R_8$ are the same or different and each a halogen atom, a hydrogen atom or a hydrocarbon group having 1 to 12 carbon atoms, and $R_9$ is an alkylene group having 3 to 8 carbon atoms.

5. The process for producing an aromatic polycarbonate according to claim 1, wherein the hydrolyzable halogen is derived from a catalyst used in the decarbonylation reaction of the aromatic oxalic acid diester.

6. The process for producing an aromatic polycarbonate according to claim 1, wherein the aromatic carbonic acid diester is obtained through the decarbonylation reaction of the aromatic oxalic acid diester represented by the above general formula (1), using a combination of an organic phosphorus compound and a halogen compound, or a halogen-containing organic phosphorus compound, as a catalyst.

7. The process for producing an aromatic polycarbonate according to claim 1, wherein the ester interchange reaction is carried out in the presence of at least one catalyst selected from the group consisting of alkali metal compounds, alkaline earth metal compounds and nitrogen-containing basic compounds.

8. The process for producing an aromatic polycarbonate according to claim 1, wherein an alkali metal compound and an alkaline earth metal compound are used as catalysts in a total equivalent amount of $1\times10^{-8}$ to $5\times10^{-5}$, based on 1 mole of the aromatic dihydroxy compound in the ester interchange reaction.

9. The process for producing an aromatic polycarbonate according to claim 1, wherein a nitrogen-containing basic compound is used as a catalyst in an equivalent amount of $1\times10^{-5}$ to $1\times10^{-3}$ based on 1 mole of the aromatic dihydroxy compound in the ester interchange reaction.

10. The process for producing an aromatic polycarbonate according to claim 1, wherein the ester interchange reaction is carried out at a temperature of 160 to 300° C.

11. The process for producing an aromatic polycarbonate according to claim 1, wherein the aromatic carbonic acid diester is obtained through the decarbonylation reaction of the aromatic oxalic acid diester and subjected to a contact treatment with hot water heated to a temperature higher than the melting point of the aromatic carbonic acid diester.

12. The process for producing an aromatic polycarbonate according to claim 11, wherein the hot water has a pH of 8 to 10.

13. The process for producing an aromatic polycarbonate according to claim 11, wherein purification by distillation is carried out before or after the above contact treatment with hot water.

14. An aromatic carbonic acid diester obtained through the decarbonylation reaction of the aromatic oxalic acid diester represented by the following general formula (1):

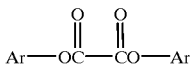

(1)

wherein two Ar's are the same or different aromatic hydrocarbon groups having 6 to 14 carbon atoms, and contains 5 ppm or less of hydrolyzable halogen.

15. The aromatic carbonic acid diester of claim 14 which is used for the production of an aromatic polycarbonate.

16. An aromatic polycarbonate obtained through an ester interchange reaction between the aromatic carbonic acid diester of claim 14 and the aromatic dihydroxy compound.

* * * * *